United States Patent [19]
Magnin

[11] Patent Number: 4,867,167
[45] Date of Patent: Sep. 19, 1989

[54] METHOD AND APPARATUS FOR DETERMINING AND DISPLAYING THE ABSOLUTE VALUE OF QUANTITATIVE BACKSCATTER

[75] Inventor: Paul A. Magnin, Andover, Mass.

[73] Assignee: Hewlett-Packard Company, Palo Alto, Calif.

[21] Appl. No.: 213,407

[22] Filed: Jun. 30, 1988

[51] Int. Cl.[4] ............................................. A61B 8/00
[52] U.S. Cl. .................................. 128/660.06; 73/599; 128/661.07
[58] Field of Search ...................... 128/660.06, 660.07, 128/661.07–661.10; 73/599, 602

[56] References Cited

U.S. PATENT DOCUMENTS

| | | | |
|---|---|---|---|
| 4,470,303 | 9/1984 | O'Donnell | 73/602 |
| 4,509,524 | 4/1985 | Miwa | 128/660.06 |
| 4,688,428 | 8/1987 | Nicolos | 73/602 |
| 4,803,994 | 2/1989 | Burke | 128/660.06 |

OTHER PUBLICATIONS

Shung, K. K. et al, "Scattering of Ultrasound by Blood", IEEE BME Trans., vol. 23, No. 6, pp. 460–467, Nov. 1976.

Perez, J. E. et al, "Applicability of UTS Tissue Characterization for Longitudinal Assessment & Differentiation of Calcification and Fibrosis in Cardiomyopathy", JACC, vol. 4, No. 1, Jul. 1984, pp. 88–95.

Fei, D. Y. et al, "Ultrasonic Backscatter from Borine Tissues: Variation with Pathology", Jrnl. Acoust. Soc. Amer., 81(1), Jan. 1987, pp. 166–177.

Primary Examiner—Francis Jaworski
Attorney, Agent, or Firm—Frank Perillo

[57] ABSTRACT

This invention teaches method and apparatus for determining backscatter attenuation, for utilizing backscatter attenuation to determine the absolute value of quantitative backscatter from a selected point of the body and/or displaying the absolute value of quantitative backscatter in a unique way. More particularly, backscatter from a selected point in the body resulting from a transmitted ultrasonic signal is detected and the quantitative value of the backscatter signal determined. The invention then determines the backscatter attenuation for moving blood at a particular point which is close to the selected point. The determined backscatter attenuation for blood is then utilized to perform an attenuation correction on the detected backscatter signal, thereby providing the absolute value of quantitative backscatter. The determined absolute value of quantitative backscatter may be color mapped on a display device by, for example, utilizing the absolute value of quantitative backscatter to control at least the color and intensity of the portion of the display imaging the selected point.

30 Claims, 1 Drawing Sheet

METHOD AND APPARATUS FOR DETERMINING AND DISPLAYING THE ABSOLUTE VALUE OF QUANTITATIVE BACKSCATTER

FIELD OF THE INVENTION

This invention relates to ultrasonic scanning systems and more particularly to method and apparatus for determining backscatter attenuation, for utilizing backscatter attentuation to determine the absolute value of the quantitative backscatter for a selected point of the body, and/or for displaying the absolute value of the quantitative backscatter in a unique way.

BACKGROUND OF THE INVENTION

For many years, ultrasonic scanning systems have been utilized in medical and other applications to obtain images of body or machine portions not visible to the human eye. By use of well-known Doppler techniques, an indication of fluid flow, such as blood flow, within the scan area may also be obtained. More recently, proposals have been made to measure the power of the backscatter (i.e., the power of the echo signal in a direction 180° to the direction of the incident ultrasonic signal) for various diagnostic purposes. For example, in an article entitled "Ultrasonic Characterization of Myocardium" in the September/October 1985 issue of *Progress in Cardiovascular Disease,* the quantitative relationship between the power of the backscatter of an ultrasonic signal and the condition of myocardium is discussed. In particular, the article discusses detecting myocardial ischemia (i.e., a lack of blood to the heart muscle) by viewing the absolute value of quantitative backscatter from the heart muscle. The absolute value of quantitative backscatter received from the heart muscle has a rhythmic variation of about 4 dB when the heart is normal. However, when the heart muscle is experiencing myocardial ischemia, the variations in power are blunted and, more important, the absolute value of the received power is perceptibly higher than when the heart muscle is normal. By detecting these changes in absolute value, it may be possible to quickly determine whether a patient has experienced or is experiencing a heart attack as well as its extent, something which may take several days of analysis using current techniques.

However, the above article does not suggest how quantitative backscatter may be determined. An article entitled "A Real-Time Integrated Backscatter Measurement System for Quantitative Cardiac Tissue Characterization", published in the January 1986 issue of *I.E.E.E., Transactions on Ultrasonic Ferroelectrics and Frequency Control,* 1 Vol. UFFC-33, No. 1, does describe an apparatus for obtaining quantitative backscatter signals. However, while the system described in this paper is capable of measuring backscatter power, it does not provide a true indication of the absolute value of quantitative backscatter, since it does not take into account attenuation of the transmitted signal from the ultrasonic transducer to the cardiac muscle or other point in the body at which the quantitative backscatter determination is to be made, and does not take into account the attenuation of the backscatter signal from this point. When used in this application, the term "point" shall be considered to be a small site, sample volume or resolution volume in the body. A point may, for example, appear as a single pixel in the display image of the scanned body area. While an estimated attenuation factor may be utilized to obtain a rough determination of quantitative backscatter, the accuracy of a quantitative backscatter determination made in this way may not be adequate for various diagnostic purposes such as, for example, for detecting myocardial ischemia, where the difference in absolute value for healthy and unhealthy tissue may not be great. For example, in the case of myocardial ischemia, the difference in absolute value of quantitative backscatter between a clearly healthy muscle tissue and one clearly undergoing myocardial ischemia, may be only 4 dB. A need therefore exists for a reliable method and apparatus for determining attenuation of backscatter signals, preferably in vivo, and for applying such determined attentuation to obtain the absolute value of quantitative backscatter for a given point in a subject's body.

Once the absolute value of quantitative backscatter has been determined, it is necessary that this information be displayed or otherwise provided to the physician or other health professional performing the procedure in a manner which will permit a determination as to the health of the patient to be quickly and accurately observed, and to quickly and accurately identify areas where potential problems exist. Methods and apparatus for displaying such information to achieve these objectives have not heretofore been known or available.

SUMMARY OF THE INVENTION

In accordance with the above, this invention provides method and apparatus for use in an ultrasonic scanning system of a type wherein an ultrasonic signal having a given voltage is transmitted toward selected points of a subject's body, and backscatter from the selected points is detected and measured. The method and apparatus detects the quantitative value of the backscatter signal received from a selected point, and determines the backscatter attenuation for moving blood at a particular point which is close to the selected point. The determined backscatter attenuation for the blood is then utilized to perform an attenuation correction on the detected backscatter signal, thereby providing the absolute value of quantitative backscatter.

For the preferred embodiment, the backscatter attenuation for moving blood is obtained by determining the Doppler spectrum of moving blood at a particular point in the body closely adjacent to the selected point, integrating the Doppler spectrum over a selected frequency range, and utilizing the results of the integration to determine the blood backscatter attenuation for the particular point. Since the selected and particular points are very close, an assumption may be made that the attenuation for both points is the same or a factor may be added to the determined attenuation value to correct for the space between the points. The frequency range over which the integration is performed is preferably from the positive Nyquist frequency to the negative Nyquist frequency, and preferably the low frequencies in the middle of this range, which may result from something other than blood movement, are filtered out or otherwise removed.

The determined absolute value of quantitative backscatter may be color-mapped on a display means and, in particular, the determined absolute value of quantitative backscatter at a given point may be utilized to control at least the color and intensity of the portion of the display imaging the selected point. Color may be considered to be made up of hue (dominant frequency) and saturation (purity or bandwidth) while intensity represents the strength of the color. While for a preferred embodiment, a ROM or other suitable memory device is provided which is addressed in response to the absolute value of quantitative backscatter values and reads out a corresponding color and intensity in response to such input value, the color-mapping function could be performed by other circuitry having the desired transfer function. Thus, if a first absolute value were considered healthy, a second absolute value unhealthy, with values in between having particular significance depending on their closeness to the first or second value, the system could cause a display of a first color at the appropriate place on the display if the absolute value of quantitative backscatter at the corresponding point in the body is of the first value, a display of a second color and intensity, indicating an unhealthy state, if the determined absolute value equals the second value, and a display of a selected color and/or intensity for each determined absolute value intermediate the first and second absolute values. Alternatively, the color of the display could remain constant, with intensity varying continuously in response to absolute values between the first and second values.

The foregoing and other objects, features and advantages of the invention will be apparent from the following more particular description of a preferred embodiment of the invention as illustrated in the accompanying drawing.

IN THE DRAWING

The FIGURE is a block schematic diagram of a preferred embodiment of the invention.

DETAILED DESCRIPTION

Figure 1:
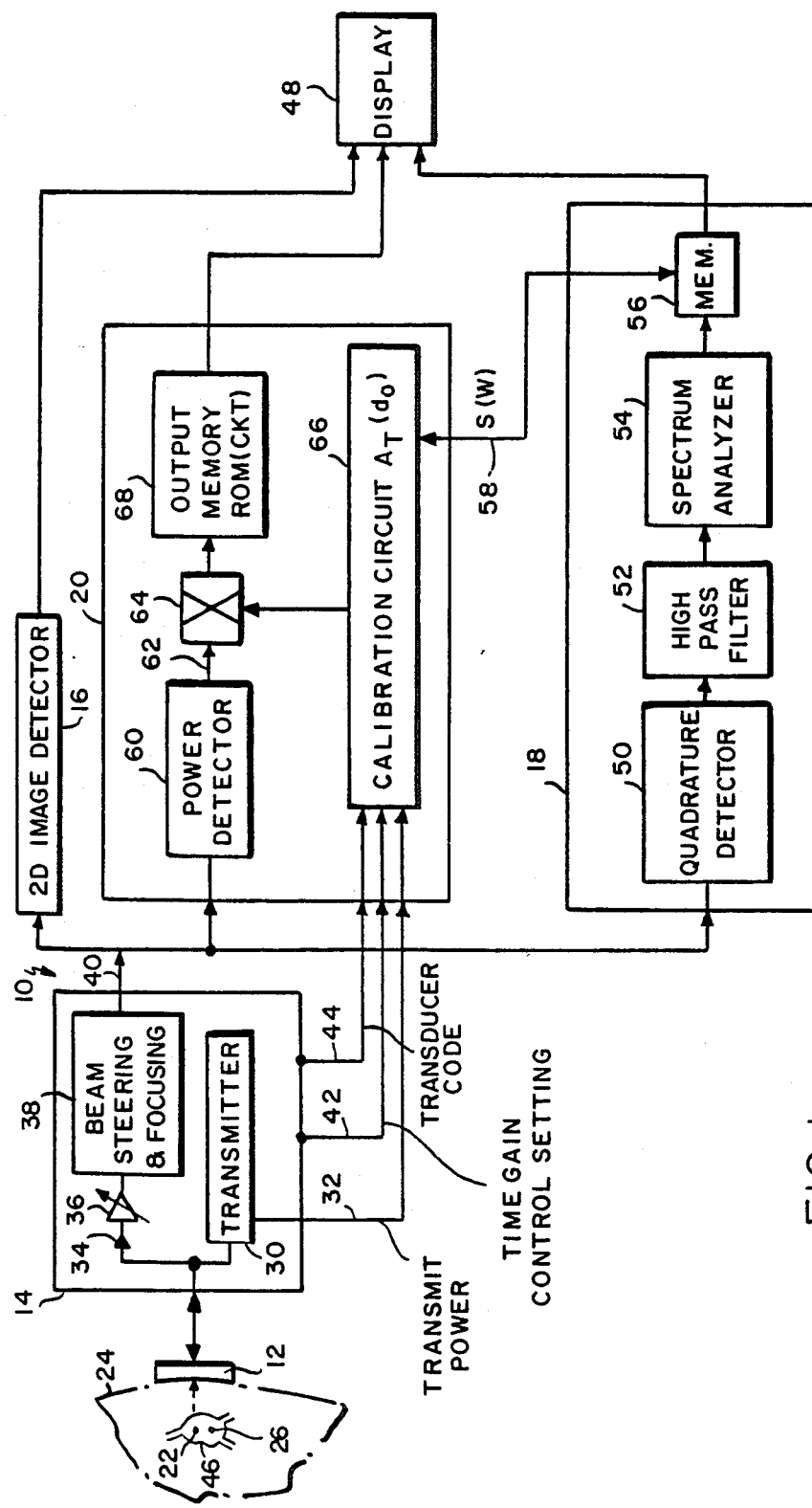

Referring to the FIGURE, the system 10 includes a conventional ultrasonic transducer 12, conventional beam transmission and receiving circuity 14, conventional ultrasonic 2D image detector circuitry 16, conventional Doppler flow detector circuitry 18 and quantitative image detection and display control circuitry 20. The teachings of this invention are, for the most part, incorporated in the circuitry 20.

In general, the system 10 is attempting to determine the quantitative backscatter for, for example, a selected point 22 on the heart muscle of a patient 24 in order to determine if the heart muscle is experiencing myocardial ischemia and thus whether the patient is experiencing or has experienced a heart attack. However, while the relative power of the backscatter signal for point 22 may be detected, the absolute value of the backscatter signal cannot be determined without knowing the amount by which the transmitted beam is attenuated in the body in traveling from transducer 12 to point 22 and the amount by which the backscatter signal is attenuated by the body between point 22 and transducer 12; but, since the scattering efficiency of body tissue varies with the health of the tissue and there are also significant variations in the signal attenuation caused by body tissue, it is not possible to accurately measure this attenuation. As a result, in the past, the best that could be done was to estimate this attenuation (using some apriori assumptions about its value and frequency dependence in certain tissue) in determining the absolute value of the quantitative backscatter (i.e. the absolute value of the backscatter power).

This invention overcomes the problem indicated above by taking advantage of the fact that the hematocrit (i.e. the volume or percentage of red blood cells in blood) is fairly constant, being roughly 41% for males and roughly 39% for females, or can be easily measured if necessary. This permits the backscatter efficiency for blood (Bs), which efficiency varies with the center frequency, bandwidth and defraction pattern for a given transducer, to be premeasured at various depths for a given transducer. The measured Bs values at various depths ($d_o$) may then be stored in the system for subsequent use. Therefore, the attenuation to and from a blood pool at a point, for example the point 26, closely adjacent to the point 22, may be determined by detecting backscatter power from the blood pool. Since the points 22 and 26 are closely adjacent (the spacing is greatly exaggerated in the figure for clarity and the points 22 and 26 would in practice normally be separated by approximately 1 cm), the body tissue between each of these points and transducer 12 is roughly the same, and therefore the attenuation determined for the point 26 may be utilized as the attentuation value for determining the absolute value of the quantitative backscatter.

Alternatively, an attenuation ($A'_T(d_o)$) may be determined by $A'_T(d_o) = A_T(d_o) d_f / d_o$ (where $A_T(d_o)$ is the determined attenuation, $d_f$ is the distance to tissue of interest and $d_o$ is the distance to point 26) and this corrected attenuation might be substituted for the determined attenuation to improve accuracy. Instead of computing $A'(d_o)$ as above where it is assumed that attenuation is constant over the area of the body being scanned, in some applications where the attenuation in the area of points 22 and 26 is different from that in other areas, an estimated value for this attenuation over the short distance ($d_f - d_o$) may be added or substrated from $A_T(d_o)$ to perform the correction.

However, the scatter from blood is less than that from tissue, resulting in it being very difficult to accurately measure the backscatter from blood in the presence of time and lateral sidelobe artifacts from nearby tissue which return to the transducer at the same time. This makes it difficult to distinguish backscatter obtained from blood and that obtained from tissue.

In accordance with the teachings of this invention, this problem is overcome by taking advantage of the fact that blood moves in the body and that standard Doppler techniques are available for detecting this movement while, except for relatively low frequency movements resulting from heart movements and the like, tissue is substantially stationary. Therefore, by integrating the voltage spectrum of the Doppler signal to obtain the power spectrum and filtering out low frequency signals which may result from tissue movement (for example, signals inside of 200 Hz), quantitative backscatter received from blood may be differentiated from backscatter received from tissue and the attenuation between the scanned blood at a particular point, for example point 26, and the transducer in both directions (sometimes hereinafter referred to as the "blood backscatter attenuation") may be determined. More particularly, the following relationships may be utilized to determine the blood backscatter attenuation:

$$\text{Power into body} \cdot \frac{\text{gain}}{\text{attenuation}} = \quad (1)$$

-continued $$\int_{t_1}^{t_2} [V_T(a) \cdot H_T(t-a)]^2 da \cdot \overset{\text{normalized}}{\underset{\text{from blood}}{\text{power scattered}}} \cdot \overset{\text{blood}}{\underset{\text{efficiency}}{\text{scattering}}} \quad (2)$$

$$\frac{G(d_o)}{A_T(d_o)} = \frac{\int_{-Nq}^{+Nq} S^2(w)dw}{D_g} B_s$$

Solving equation (2) for attenuation gives:

$$A_T(d_o) = \frac{\frac{G(d_o)D_g}{B_s} \int_{t_1}^{t_2} [V_T(a) \cdot H_T(t-a)]^2 da}{\int_{-Nq}^{+Nq} S^2(w)dw} \quad (3)$$

In the equations indicated above:
$A_T(d_o)$ = blood backscatter attenuation at distance $d_o$
$G(d_o)$ = beam scanner gain for depth (distance) $d_o$
$D_g$ = additional Doppler gain
$B_s$ = blood scattering efficiency
$V_T(t)$ = the transmitted voltage at time (t)
$H_T(t)$ = the transducer impulse response
$S(w)$ = voltage spectrum of Doppler signal
t1 = the beginning of the ultrasonic transmission
t2 = the end of ultrasonic transmission
Nq = the Nyquist frequency The attenuation determined utilizing equation (3) may then be utilized either directly or with a correction factor (f) to modify the detected quantitative backscatter from point 22 in order to determine the absolute value of quantitative backscatter for this point.

The circuit shown in the FIGURE implements the procedure described above. In particular, circuit 14 includes a transmitter 30 the transmission voltage and power (as given by the first term of equation 2) of which are known (or can be determined) and an indication of which appears on line 32. The signal from transmitter 30 is applied to transducer 12 to cause the ultrasonic beam output. The backscatter signal received by transducer 12 is applied through a preamplifier 34 to a timegain control circuit 36. Circuit 36 is a standard circuit which may, for example, be manually controlled to vary the amplitude of the output to aid in compensating for the attenuation which occurs during the time between the transmitted and received signals, this time difference being a function of the depth of the point 22 at which the beam is being focussed. The output from gain control circuit 36 is applied to a standard beam steering and focusing circuit 38, the outputs from which are applied to circuits 16, 18 and 20 over lines 40. In addition to output lines 32 and 40, there is also an output line 42 from circuit 14 which contains a signal proportional to the gain setting of circuit 36 and an output line 44 which contains a signal indicative of the transducer impulse response ($H_T(t)$). The transducer impulse response is fixed for a given transducer 12.

The signals on line 40 are applied to the 2D image detector 16, resulting in an image of the portion of body 24, for example, heart 46, being displayed on display 48. Display 48 may, for example, be a conventional cathode ray tube monitor. The manner in which circuit 16 causes an image to be generated on display 48 is conventional and does not form part of the present invention.

Similarly, the signals on line 40 are applied to Doppler circuitry 18 to cause a Doppler spectrum of the moving blood to be drawn on display 48. The manner in which this is accomplished is also conventional and involves passing the received signal through a quadrature detector 50, a high-pass filter 52 and a spectrum analyzer 54. The voltage spectrum of Doppler signal at the output from analyzer 54 is stored in memory 56 and is applied both to control the display on display 48 and to circuit 20 for reasons which will be discussed shortly.

While the operation of circuit 18 is conventional, two points should be noted about this circuit which are of particular concern with respect to this invention. First, since circuit 18 is measuring Doppler shift frequencies, and since such shifts occur only as a result of movement, an output is obtained from Doppler circuit 18 only when blood in movement is being scanned. Since in the heart area blood is not always in movement, the attenuation determination of this invention can be made only when the blood being looked at is in sufficiently rapid movement so that the frequency spectrum exceeds the frequency of filter 52. Second, the Doppler circuit includes a high-pass filter 52 which filters out low-frequency signals which might result from tissue movement such as those caused by breathing or heart beating. Therefore, the signal applied to spectrum analyzer 54 and the S(w) signal appearing on line 58 represent the frequency spectrum over the selected range without the low-frequency component.

Finally, the signal on line 40 is applied as the input to power detector circuit 60 in quantitative backscatter circuit 20. The circuit 60 generates an output on line 62 which is a function of the power received from, for example, point 22, by transducer 12. The signal on line 62 is applied as one input to multiplier circuit 64.

The other input to multiplier circuit 64 is the output from attenuation determination or calibration circuit 66. Circuit 66 receives as inputs the transmitted power signal on line 32 (or a transmitted voltage signal which circuit 66 converts to power), the time gain control value on line 42, and indicator of the transducer impulse response on line 44, and the Doppler voltage spectrum signal on line 58. The additional Doppler gain is either prewritten into the circuit 66 or is applied to this circuit over lines 58 and the bloodscatter efficiency for the patient 24 is initially entered and stored in this circuit. This value is determined for the transducer 12 for various depths as previously described and may be modified to correct for the sex hematocrit of the subject. With these inputs, circuit 66 has all of the information required to determine the blood backscatter attenuation at, for example, the point 26 and is operative to perform this calculation and to apply the determined attenuation as a second input to multiplier 64. Circuit 66 may be a special purpose circuit designed to implement equation 3, but may be a microprocessor programmed to perform this function. In the alternative, general purpose processing circuitry contained in the ultrasonic scanning system and utilized for other purposes in conjunction with this system, may also be programmed to perform the attenuation determination at appropriate points in the operation. The function of multiplier 64 may also be performed by a programmed processor in the system or by a special purpose component or circuit. The detected power multiplied by the determined attenuation provides the desired absolute value of quantitative backscatter at the output from multiplier 64.

The output from multiplier 64 is applied as the addressing input to output mapping ROM circuit 68. For a preferred embodiment, circuit 68 includes a ROM which is addressed by the absolute value of quantitative backscatter from multiplier 64, and which contains at each of its addressable positions a hue, saturation, and/or intensity (or red, blue, green intensity) which is to be displayed at the point on the image from circuit 16 being displayed on display 48 which corresponds to the point being scanned, for example, point 22. Thus, if the absolute value of quantitative backscatter from the point 22 is of a first, lower value, signifying that the heart muscle tissue being scanned is healthy, the color (i.e. hue and saturation) and intensity outputted from circuit 68 to control display 48 at the point on the image corresponding to point 22 would be of a first selected color and intensity. For example, the point on the image might be bright, deep green. Conversely, if the absolute value of quantitative backscatter applied to circuit 68 is of a second, higher value which is determined to be unhealthy, the values read out from circuit 68 might cause the display in the area corresponding to point 22 to be of a different color, for example, a deep red. Absolute values of quantitative backscatter for the selected point between the first and second values might be displayed in a manner which would result in a mixing of the colors so that, as the value moved from the healthy value to the unhealthy value, the displayed color would take on an increasing red tinge as more and more color red was mixed with the green and less and less green appeared in the color, until the second value was reached, at which the output would be completely red. A second option might be for the color to remain constant but of increasing (or decreasing) intensity as the absolute values moved from the first healthy value to the second unhealthy value. The latter option would be particularly useful with a black and white monitor with the grey scale varying from, for example, white or a light grey for healthy to black for unhealthy. Other options for varying hue, saturation and/or intensity between the two absolute values also exist. The objective in each instance is to provide a display which, when viewed by the system operator, provides a clear, quick indication of the health status of the patient with respect to the particular symptom being tested for. Outside the range between the first and second values, it is unlikely that the tissue is either healthy or infarcted and therefore a third color, for example blue, or an intensity, such as white, might be chosen for determined absolute values of quantitative backscatter of these values.

It is apparent that while the discussion above has been with respect to a single point 22 in the heart muscle of the patient 24, the system would in fact be scanning the heart and would be viewing a large number of points in succession to develop the desired image. The process described above would be repeated for each point of interest being scanned so that the final image would be of the entire area of the heart or other body organ in which a potential problem exists.

In utilizing the system shown in FIG. 1, the selection of the point 26 at which there is a pool of moving blood to be used in making the attenuation determination for a given scan point 22 may be performed by the operator on a point by point basis, or may be performed automatically. When the process is performed manually, a sample volume cursor appearing on the screen of display 48 may be moved in conventional fashion by the operator to a blood pool imaged on the screen which the operator selects as being the closest available blood pool to a point on the patient's body which is of interest. The operator may then wait until the screen indicates that the blood in that blood pool is in motion and then takes appropriate action, such as pressing a button, to cause a trigger signal to be applied to circuits 20 to cause a quantitative backscatter determination to be made for the point 22. This process would be repeated for each successive point on the heart muscle at which the operator wished for a determination to be made.

In either the manual or automatic mode, it is possible to generate the trigger signal to circuit 20 in at least two other ways. The first way is to utilize an ECG machine with a probe connected to an appropriate point on the patient's body, causing an output when blood in the select pool is in motion, which output functions as a trigger pulse. In the alternative, an output on line 58 from circuit 18 which exceeds a predetermined threshold at the point indicated by the cursor may be utilized as the trigger input to circuit 20. With any of the three techniques, the ultimate objective is to assure that absolute quantitative backscatter determinations are made only when the selected blood pool is in motion.

In the fully automatic mode, one of a variety of techniques could be utilized in vivo to determine the appropriate blood pool for making an attenuation determination for each selected point 22. For example, the points 22 of interest with respect to a given patient could be manually loaded into the system by the operator by use of the cursor on display 48, a keyboard or other suitable means. As the beam scanned these points, the system would also be monitoring the output from circuit 18 to find the blood pool most closely adjacent to each selected point. Since a determination from circuit 18 could be made only when blood was in motion, a number of scans would be required to make the determination, since the closest blood pool to a selected point might not be in motion during a given scan. Thus, the closest point during a given scan could be indicated and stored and this point could be compared against the closest point determined during a subsequent scan with a new value being substituted if a later point is determined to be closer than the stored point for a given selected point 22. As with previous functions described, the automatic mode of operation indicated above could be implemented in either special purpose hardware or with a programmed processor.

In addition, while output mapping circuit 68 has been indicated as being a table lookup ROM or other memory device for the preferred embodiment of the invention, it is apparent that the output mapping could be implemented with other circuitry, either hardware or software, having the desired transfer function. Thus, a given output voltage from multiplier 64 could be applied through suitable analog circuitry, gating circuitry, or the like to cause output voltages from circuit 68 to display 48 which would control the color and intensity of this display.

Further, while the discussion above has been with respect to diagnosing heart problems in general, and myocardial ischemia in particular, the measurement, calibration and display techniques disclosed could be utilized for detecting and diagnosing problems of other bodily organs which exhibit distinctive quantitative backscatter patterns.

Finally, while a particular configuration of components has been disclosed for the preferred embodiment, it is apparent that the teachings of this invention could be practised utilizing other hardware and/or software adapted to perform the indicated functions. Thus, while the invention has been shown and described above with reference to a preferred embodiment, the foregoing and other changes in form and detail may be made therein by one skilled in the art without departing from the spirit and scope of the invention.

What is claimed is:

1. In an ultrasonic scanning system of the type wherein an ultrasonic signal having a given voltage is transmitted towards selected points of a subject's body and backscatter from the selected points is detected and measured, there being a predetermined blood scattering efficiency for the subject, apparatus for determining the backscatter attenuation for a selected point of the body comprising:
   means for determining the Doppler voltage spectrum of moving blood at a particular point in the body closely adjacent to the selected point;
   means for integrating said Doppler voltage spectrum over a selected frequency range;
   means for utilizing the output of the integrating means, said blood scattering efficiency and said given voltage to determine the blood backscatter attenuation for the particular point; and
   means for utilizing the determined blood backscatter attenuation in determining the backscatter attenuation for the selected point.

2. Apparatus as claimed in claim 1 including means for removing selected low frequency portions of the Doppler voltage spectrum prior to application to said means for integrating; and
   wherein said selected frequency range is from the positive Nyquist frequency to the negative Nyquist frequency.

3. Apparatus as claimed in claim 2 wherein said blood backscatter attenuation is calculated utilizing the equation $$A_T(d_o) = \frac{\frac{G(d_o)D_g}{B_s} \int_{t_1}^{t_2} [V_T(a) H_T(t - a)]^2 da}{\int_{-Nq}^{+Nq} S^2(w)dw}$$

In the equations indicated above:
   $A_T(d_o)$ = blood backscatter attenuation at distance $d_o$
   $G(d_o)$ = beam scanner gain for depth (distance) $d_o$
   $D_g$ = additional Doppler gain
   $B_s$ = blood scattering efficiency
   $V_T(t)$ = the transmitted voltage at time (t)
   $H_T(t)$ = the transducer impulse response
   $S(w)$ = voltage spectrum of Doppler signal
   t1 = the beginning of the ultrasonic transmission
   t2 = the end of ultrasonic transmission
   Nq = the Nyquist frequency.

4. Apparatus as claimed in claim 1 wherein said utilizing means utilizes the determined blood backscatter attenuation directly as the backscatter attenuation for the selected point.

5. Apparatus as claimed in claim 1 wherein said means for utilizing includes means for adjusting the determined blood backscatter attenuation to compensate for the distance between the selected and predetermined points in the direction to the ultrasonic signal.

6. In an ultrasonic scanning system of the type wherein an ultrasonic signal is transmitted towards selected points of a subject's body and backscatter from the selected points is detected and measured, apparatus for generating a signal which is a function of the absolute value of the quantitative backscatter from a selected point of the body comprising:
   means for detecting the quantitative value of the backscatter signal received from the selected point;
   means for determining the backscatter attenuation for moving blood at a particular point which is close to the selected point; and
   means for utilizing the backscatter attenuation output from the determining means to perform an attenuation correction on the detected backscatter signal;
   whereby the absolute value of the quantitative backscatter may be determined.

7. Apparatus as claimed in claim 6 wherein the transmitted ultrasonic signal has a given voltage, wherein there is a predetermined blood scattering efficiency for the subject, and wherein said means for determining includes means for determining the Doppler voltage spectrum of moving blood at said particular point; and
   including means for integrating said Doppler voltage spectrum over a selected frequency range;
   means for utilizing the output of the integrating means, said blood scattering efficiency and said given voltage to determine the blood backscatter attenuation for the particular point; and
   means for utilizing the determined blood backscatter attenuation in determining the backscatter attenuation for the selected point.

8. Apparatus as claimed in claim 7 including means for removing selected low frequency portions of the Doppler spectrum prior to application to said means for integrating; and
   wherein said selected frequency range is from the positive Nyquist frequency to the negative Nyquist frequency; and
   wherein said blood backscatter attenuation is calculated utilizing the equation $$A_T(d_o) = \frac{\frac{G(d_o)D_g}{B_s} \int_{t_1}^{t_2} [V_T(a) H_T(t - a)]^2 da}{\int_{-Nq}^{+Nq} S^2(w)dw}$$

where:
   $A_T(d_o)$ = blood backscatter attenuation at distance $d_o$
   $G(d_o)$ = beam scanner gain for depth (distance) $d_o$
   $D_g$ = additional Doppler gain
   $B_s$ = blood scattering efficiency
   $V_T(t)$ = the transmitted voltage at time (t)
   $H_T(t)$ = the transducer impulse response
   $S(w)$ = voltage spectrum of Doppler signal
   t1 = the beginning of the ultrasonic transmission
   t2 = the end of ultrasonic transmission
   Nq = the Nyquist frequency.

9. Apparatus as claimed in claim 6 wherein said means for utilizing utilizes the determined blood backscatter attenuation directly as the backscatter attenuation for the selected point.

10. Apparatus as claimed in claim 6 wherein said means for utilizing includes means for adjusting the determined blood backscatter attenuation to compensate for the distance between the selected and predetermined points in the direction of the ultrasonic signal.

11. Apparatus as claimed in claim 6 wherein said predetermined point is selected manually.

12. Apparatus as claimed in claim 6 including means for automatically selecting the predetermined point to be used for each selected point.

13. Apparatus as claimed in claim 6 including means for color mapping the determined absolute value of the quantitative backscatter.

14. Apparatus as claimed in claim 13 including a display means; and
wherein said color mapping means includes means responsive to said determined absolute value for controlling at least the color and intensity of at least a selected portion of the display on said display means.

15. Apparatus as claimed in claim 14 wherein said means for controlling includes memory means for storing a table of absolute values and corresponding color and intensity information, and means responsive to a detected absolute value of quantitative backscatter for reading out the corresponding color and intensity information to control the display.

16. Apparatus as claimed in claim 14 wherein the system is being used for diagnostic purposes, wherein first absolute values of quantitative backscatter for certain portions of the body are regarded as healthy and second absolute values are regarded as unhealthy, and wherein said means for controlling is operative in response to said determined absolute value being equal to a first absolute value for causing the at least selected portion of the display to be of a first color and of a first selected intensity, is operative in response to said determined absolute value being equal to a second absolute value for causing the selected portion of the display to be of a second different color and a second intensity, which second intensity may be the same as the first intensity, and is operative in response to the determined absolute value being between the first and second absolute values for controlling at least the color or intensity of the display portion in a predetermined manner.

17. Apparatus as claimed in claim 16 wherein the means for controlling is operative when the detected absolute value is between the first and second absolute values to control the color of the display portion to be a color between the first and second color, the displayed color varying as a function of the difference between the detected absolute value and the first and second absolute values respectively.

18. Apparatus as claimed in claim 14 wherein the system is being used for diagnostic purposes, wherein first absolute values of quantitative backscatter for certain portions of the body are regarded as healthy and second absolute values are regarded as unhealthy, and wherein said means for controlling is operative to control the intensity of the display such that the intensity varies substantially uniformly as the detected absolute value varies from the first absolute value to the second absolute value.

19. In an ultrasonic scanning system of the type wherein an ultrasonic signal is transmitted towards selected points of a subject's body and backscatter from the selected points is detected and measured, apparatus for generating a color map image, at least the color or intensity of which conveys diagnostic information concerning the subject, comprising:

means for determining the absolute value of the quantitative backscatter signal received from a selected point;

a display means;

memory means storing a table of absolute values and corresponding color and intensity information;

means responsive to a determined absolute value of quantitative backscatter for reading out the corresponding color and intensity information to control the display;

first absolute values of quantitative backscatter for certain portions of the body being regarded as healthy and second absolute values being regarded as unhealthy;

means responsive to the determined value being equal to the first absolute value for reading out corresponding first color and intensity values to control at least a portion of the display at said display means, whereby the display indicates that the subject is healthy, responsive to the determined value being equal to the second absolute value for reading out corresponding second color and intensity values to control said display, whereby the display indicates that the subject has a particular health problem, and responsive to the determined value being between the first and second values for reading out corresponding color and intensity values to control the display to indicate in a predetermined manner the relative health of the subject.

20. In an ultrasonic scanning system of the type wherein an ultrasonic signal having a given voltage is transmitted towards selected points of a subject's body and backscatter from the selected points is detected and measured, there being a predetermined blood scattering efficiency for the subject, a method for determining the attenuation of the backscatter from a selected point of the body comprising the steps of:

determining the Doppler spectrum of moving blood at a particular point in the body closely adjacent to the selected point;

integrating said Doppler spectrum over a selected frequency range;

utilizing the output of the integrating step, said blood scattering efficiency and said given voltage to determine the blood backscatter attenuation for the particular point; and utilizing the determined blood backscatter attenuation to determine the backscatter attenuation for the selected point.

21. A method as claimed in claim 20 wherein said selected frequency range is from the positive Nyquist frequency to the negative Nyquist frequency with selected low frequencies removed; and wherein said blood backscatter attenuation is calculated utilizing the equation $$A_T(d_o) = \frac{\frac{G(d_o)D_g}{B_s} \int_{t_1}^{t_2} [V_T(a) H_T(t-a)]^2 da}{\int_{-Nq}^{+Nq} S^2(w) dw}$$

where:

$A_T(d_o)$ = blood backscatter attenuation at distance $d_o$
$G(d_o)$ = beam scanner gain for depth (distance) $d_o$
$D_g$ = additional Doppler gain
$B_s$ = blood scattering efficiency
$V_T(t)$ = the transmitted voltage at time (t)

$H_T(t)$ = the transducer impulse response
$S(w)$ = voltage spectrum of Doppler signal
$t1$ = the beginning of the ultrasonic transmission
$t2$ = the end of ultrasonic transmission
$Nq$ = the Nyquist frequency.

22. A method as claimed in claim 20 wherein said utilizing step includes the step of adjusting the determined blood backscatter attenuation to compensate for the distance between the selected and predetermined points in the direction of the ultrasonic signal.

23. In an ultrasonic scanning system of the type wherein an ultrasonic signal having a given voltage is transmitted towards selected points of a subject's body and backscatter from the selected points is detected and measured, a method for generating a signal which is a function of the absolute value of the quantitative backscatter from a selected point of the body comprising the steps of:

detecting the quantitative value of the backscatter signal received from the point;

determining the backscatter attenuation for moving blood at a particular point which is closely adjacent to the selected point;

utilizing the backscatter attenuation output from the determining step to perform an attenuation correction on the detected backscatter signal; and whereby the absolute value of the quantitative backscatter may be determined.

24. A method as claimed in claim 23 wherein the transmitted ultrasonic signal has a given voltage, wherein there is a predetermined bloodscattering efficiency for the subject, and wherein said determining step includes the steps of determining the Doppler voltage spectrum of moving blood at said particular point, integrating said Doppler voltage spectrum over a selected frequency range, and utilizing the output of the integrating step, said blood scattering efficiency and said given voltage to determine the blood backscatter attenuation for the particular point.

25. A method as claimed in claim 24 wherein said selected frequency range is from the positive Nyquist frequency to the negative Nyquist frequency with certain low frequencies removed; and wherein said blood backscatter attenuation is calculated utilizing the equation $$A_T(d_o) = \frac{\frac{G(d_o)D_g}{B_s} \int_{t_1}^{t_2} [V_T(a) H_T(t-a)]^2 da}{\int_{-Nq}^{+Nq} S^2(w) dw}$$

where:
$A_T(d_o)$ = blood backscatter attenuation at distance $d_o$
$G(d_o)$ = beam scanner gain for depth (distance) $d_o$
$D_g$ = additional Doppler gain
$B_s$ = blood scattering efficiency
$V_T(t)$ = the transmitted voltage at time (t)
$H_T(t)$ = the transducer impulse response
$S(w)$ = voltage spectrum of Doppler signal
$t1$ = the beginning of the ultrasonic transmission
$t2$ = the end of ultrasonic transmission
$Nq$ = the Nyquist frequency.

26. A method as claimed in claim 23 including the step of adjusting the determined blood backscatter attenuation to compensate for the distance between the selected and predetermined points in the direction of the ultrasonic signal.

27. A method as claimed in claim 23 including the step of manually selecting the predetermined point to be used for each selected point.

28. A method as claimed in claim 23 including the step of automatically selecting the predetermined point to be used for each selected point.

29. A method as claimed in claim 23 including the step of color mapping the determined absolute value of quantitative backscatter.

30. A method as claimed in claim 29 wherein the system is being used for diagnostic purposes, wherein first absolute values of quantitative backscatter for certain portions of the body are regarded as healthy and second absolute values are regarded as unhealthy; and including the steps of imaging the scanned portion of the subject's body on a display means;

causing the portion of the displayed image corresponding to the selected point to be of a first color and intensity in response to the absolute value of quantitative backscatter for the point being equal to the first absolute value;

causing the portion of the displayed image corresponding to the selected point to be of a second color and intensity in response to the absolute value of quantitative backscatter for the point being equal to the second absolute value; and causing the color and/or intensity of the displayed image at the selected point to be between the first and second color and/or intensity in response to the absolute value of quantitative backscatter at the selected point being between the first and second values.

* * * * *